United States Patent
Andersson et al.

[11] Patent Number: 5,856,346
[45] Date of Patent: Jan. 5, 1999

[54] SHORT-ACTING DIHYDROPYRIDINES

[75] Inventors: Kjell Hjalmar Andersson, Fjärås; Margareta Nordlander, Askim; Rolf Christer Westerlund, Mölndal, all of Sweden

[73] Assignee: Astra Aktiebolag, Sodertalje, Sweden

[21] Appl. No.: 356,224

[22] PCT Filed: Nov. 3, 1994

[86] PCT No.: PCT/SE94/01031

§ 371 Date: Dec. 14, 1994

§ 102(e) Date: Dec. 14, 1994

[87] PCT Pub. No.: WO95/12578

PCT Pub. Date: May 11, 1995

[30] Foreign Application Priority Data

Nov. 5, 1993 [SE] Sweden ................................. 9303657

[51] Int. Cl.$^6$ .......................... A61K 31/44; C07D 213/80
[52] U.S. Cl. ........................... 514/356; 546/321; 546/322
[58] Field of Search ........................... 514/356; 546/322, 546/321

[56] References Cited

U.S. PATENT DOCUMENTS 3,799,934  3/1974  Meyer et al. ........................... 546/257
4,154,839  5/1979  Wehinger et al. ........................ 514/356

FOREIGN PATENT DOCUMENTS 0 012 180 A1  10/1979  European Pat. Off. .
0 366 548 A1  5/1990  European Pat. Off. .

OTHER PUBLICATIONS

Chemical Abstracts, vol. 117(1), abst. No. 7808n, Jul. 6, 1992.

*Primary Examiner*—Alan L. Rotman
*Attorney, Agent, or Firm*—Nixon & Vanderhye

[57] ABSTRACT

Compounds of the general formula

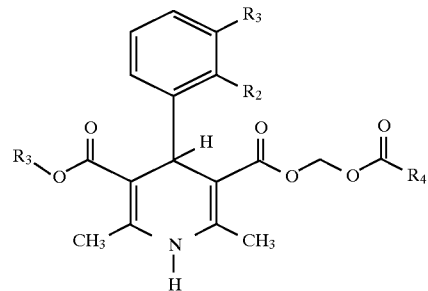

wherein $R_1$ and $R_2$ are independently selected from the group consisting of hydrogen, chloro, bromo, nitro, cyano, trifluoromethyl, and $R_3$ and $R_4$ are independently selected from straight or branched lower (1–5 carbon atoms) alkyl groups, and including all optical isomers, provided that when $R_3$ is methyl and $R_4$ is tert.-butyl, then $R_1/R_2$ are not hydrogen/hydrogen, hydrogen/2'-trifluormethyl, 2'-chloro/3'-chloro, and when $R_3$ is methyl and $R_1/R_2$ is hydrogen/3'-nitro, then $R_4$ are not methyl, ethyl, propyl, iso-propyl, tert.-butyl, processes for their preparation, pharmaceutical preparations containing them and the use of the compounds in lowering the blood pressure.

8 Claims, No Drawings

SHORT-ACTING DIHYDROPYRIDINES

FIELD OF THE INVENTION

The present invention relates to novel, potent, very short-acting calcium antagonists of the dihydropyridine type with high vascular selectivity. The compounds of the invention are very effective in lowering blood pressure, and, due to their very short duration of action, are highly efficient for obtaining steerable blood pressure control after intravenous administration. The present invention also relates to processes for preparation of these compounds as well as suitable pharmaceutical compositions for their administration. Furthermore the invention also relates to the use of the compounds of the invention for medical treatment.

BACKGROUND OF THE INVENTION

Steerable blood pressure control is of great importance in many acute clinical situations, e.g. in the majority of patients undergoing cardiac surgery, cerebral surgery, orthopedic surgery or microsurgery. Under such conditions it is often important to rapidly and safely lower blood pressure to a pre-specified level, keeping it there for a pre-determined time, and then rapidly normalizing it again.

Although some drugs are presently used in the clininc for such purpose, none of them are really adequate for efficient blood pressure control.

The drugs most commonly used for this indications are sodium nitroprusside, nitroglycerine and nicardipine. Sodium nitroprusside is an old, potent and very short-acting compound wich in most countries is the only drug available with a suitable profile of acion, i.e. mainly causing arterial dilation. However, several serious side effects limit its usefulness. The main disadvantage being the risk of cyanide intoxication. A second disadvantage is its effects on regional myocardial blood flow in patients with coronary artery disease. Nitroglycerine is also very short-acting, but has too low potency to be really effective except in high doses which also causes unwanted lowering of cardiac output. Nicardipine, which is a calcium antagonist of the dihydropyridine type, has high vascular selectivity and high potency, but the effect duration is too long, as usually is the case for this class of compounds.

Thus, there exist today a clear medical need for new short-acting, steerable antihypertensive drugs for intravenous administration. The compounds of the present invention are useful for this purpose.

PRIOR ART

Hypotensive calcium antagonists of the dihydropyridine type are now well established for prophylaxis and treatment of various cardiovascular diseases (Opic LH. Clinical use of Calcium channel antagonist Drugs. Kluwer Academic Publ. 1990. ISBN O-7923-0872-7). The main impetus in their development has been to identify safe, highly potent drugs with long duration of action. However, no efforts in the direction of developing short-acting dihydropyridines have been made.

A few compounds of similar type to those of the present invention have earlier been described (EP 0 474 129 A2; Tetrahedron Letters 32, 5805-8, (1991); Tetrahedron Letters 33, 7157–60, (1992)).

The following compounds are described:
methyl pivaloxymethyl 1,4-dihydro-2,6-dimethyl-4-(2', 3'-dichlorophenyl)-3,5-pyridinedicarboxylate,
methyl pivaloxymethyl 1,4-dihydro-2,6-dimethyl-4-(2'-trifluoromethylphenyl)-3,5-pyridinedicarboxylate,
methyl pivaloxymethyl 1,4-dihydro-2,6-dimethyl-4-phenyl-3,5-pyridinedicarboxylate
methyl pivaloxymethyl 1,4-dihydro-2,6-dimethyl-4-(3'-nitrophenyl)-3,5-pyridinedicarboxylate,
methyl isobutyroxymethyl 1,4-dihydro-2,6-dimethyl-4-(3'-nitrophenyl)-3,5-pyridinedicarboxylate,
methyl butyroxymethyl 1,4-dihydro-2,6-dimethyl-4-(3'-nitrophenyl)-3,5-pyridinedicarboxylate,
methyl propionoxymethyl 1,4-dihydro-2,6-dimethyl-4-(3'-nitrophenyl)-3,5-pyridinedicarboxylate,
methyl acetyloxymethyl 1,4-dihydro-2,6-dimethyl-4-(3'-nitrophenyl)-3,5-pyridinedicarboxylate.

These compounds were prepared in order to fascilitate the synthesis of pure enantiomers of conventional, long-acting dihydropyridines and have not been described for medical use.

1,5-Benzothiazepine derivatives have been described (EP 0 416 479 A1) for use as short-acting calcium antagonists, for treating patients with critical cardiovascular diseases.

DESCRIPTION OF THE INVENTION

It has now been found that 1,4-dihydropyridines of the general formula I:

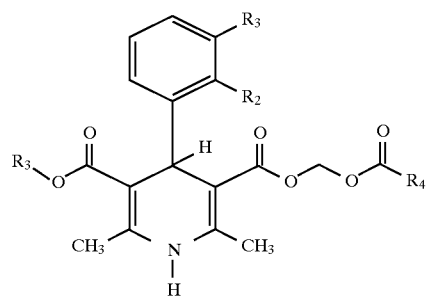

wherein $R_1$ and $R_2$ are independently selected from the group consisting of hydrogen, chloro, bromo, nitro, cyano, trifluoromethyl, and $R_3$ and $R_4$ are independently selected from straight or branched lower (1–5 carbon atoms) alkyl groups, and including all optical isomers, provided that when $R_3$ is methyl and $R_4$ is tert.-butyl, then $R_1/R_2$ are not hydrogen/hydrogen, hydrogen/2'-trifluormethyl, 2'-chloro/3'-chloro, and when $R_3$ is methyl and $R_1/R_2$ is hydrogen13'-nitro, then $R_4$ are not methyl, ethyl, propyl, iso-propyl, tert.-butyl, are effective as very short-acting, potent and vasoselective antihypertensive agents, useful for intravenous administration.

Preferred compounds of the invention are:
1) Acetoxymethyl methyl 4-(2',3'-dichlorophenyl)-2,6-dimethyl-1,4-dihydropyridine-3,5-dicarboxylate
2) Propionoxymethyl methyl 4-(2',3'-dichlorophenyl)-2,6-dimethyl-1,4-dihydropyridine-3,5-dicarboxylate
3) Butyroxymethyl methyl 4-(2',3'-dichlorophenyl)-2,6-dimethyl-1,4-dihydropyridine-3,5-dicarboxylate
4) (4S)-Butyroxymethyl methyl 4-(2',3'-dichlorophenyl)-2,6-dimethyl-1,4-dihydropyridine-3,5-dicarboxylate
5) (4R)-Butyroxymethyl methyl 4-(2',3'-dichlorophenyl)-2,6-dimethyl-1,4-dihydropyridine-3,5-dicarboxylate
6) iso-Butyroxymethyl methyl 4-(2',3'-dichlorophenyl)-2,6-dimethyl-1,4-dihydropyridine-3,5-dicarboxylate Specially preferred compounds of the invention are
1) Butyroxymethyl methyl 4-(2',3'-dichlorophenyl)-2,6-dimethyl-1,4-dihydropyridine-3,5-dicarboxylate
2) (4S)-Butyroxymethyl methyl 4-(2',3'-dichlorophenyl)-2,6-dimethyl-1,4-dyhydropyridine-3,5-dicarboxylate 3) (4R)-Butyroxymethyl methyl 4-(2',3-dichlorophenyl)-
2,6-dimethyl-1,4-dihydropyridine-3,5-dicarboxylate Method of preparation The compounds of the invention may be prepared as outlined below. However, the invention is not limited to these methods, the compounds may also be prepared as described in known art.

Method A:

The compounds of the present invention (I) can be prepared from the corresponding, suitably substituted 1,4-dihydropyridine monocarboxylic acid (II) by standard alkylation with acyloxychloromethanes in the presence of base, as outlined below.

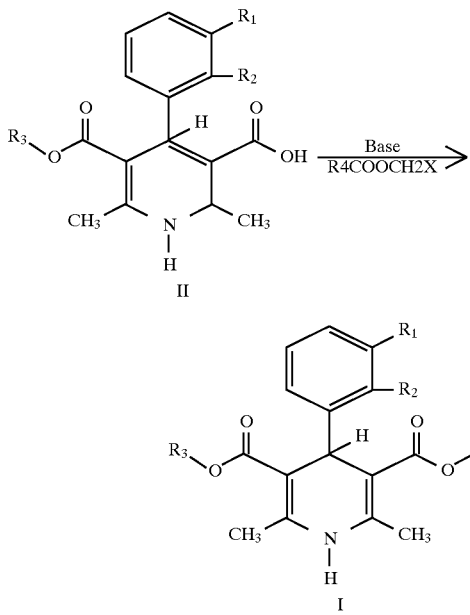

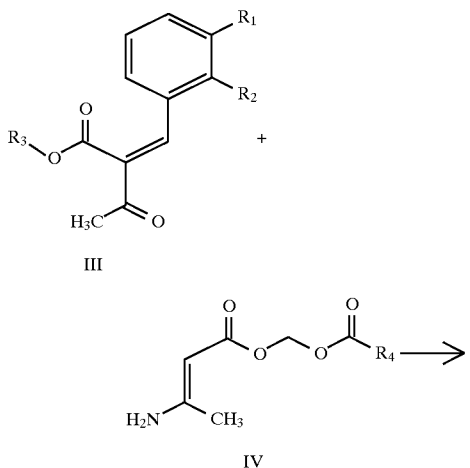

wherein $R_1$–$R_4$ have the same meaning as described above, and base is such as sodium hydride, sodium bicarbonate, triethylamine and X is a standard leaving group such as a halogen atom, tosylate or mesylate. As solvent can a polar aprotic solvent be used, such as dimethylformamide.

Method B:

The compounds of the present invention (I) can be prepared by condensating a suitable benzylidene compound (III) with an aminocrotonate (IV) as outlined below:

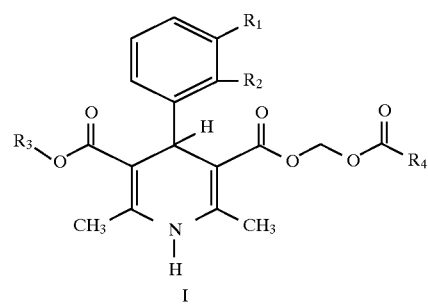

wherein $R_1$–$R_4$ have the same meaning as described above.

Method C:

The compounds of the present invention (I) can be prepared by condensating a suitable benzylidene compound (V) with an aminocrotonate (VI) as outlined below

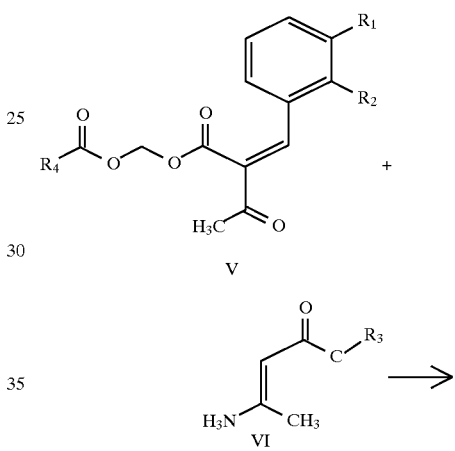

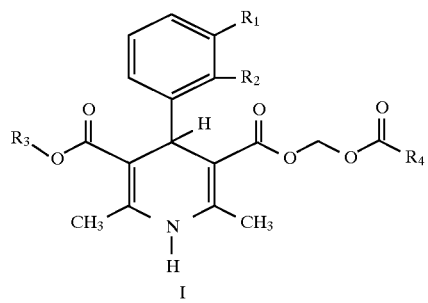

wherein $R_1$–$R_4$ have the same meaning as described above.

Method D:

The compounds of the present invention (I) can be prepared by reacting a suitable benzaldehyde (VIII) with an suitable acetoacetate (VII) and an aminocrotonate (VI) as outlined below:

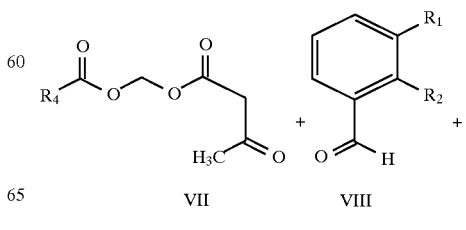

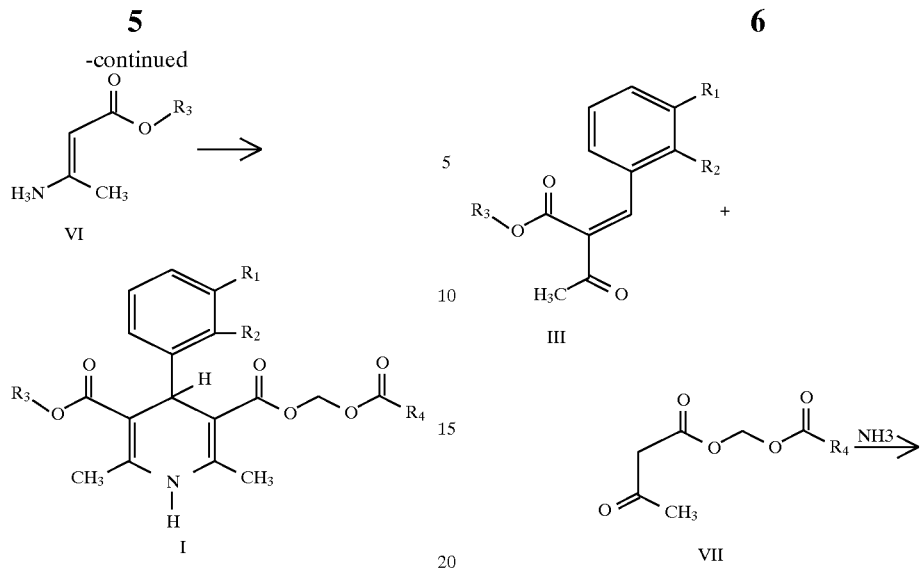

wherein $R_1$–$R_4$ have the same meaning as described above.

Method E:

The compounds of the present invention (I) can be prepared by reacting a suitable benzaldehyde (VIII) wotj an suitable acetoacetate (IX) and an aminocrotonate (IV) as outlined below:

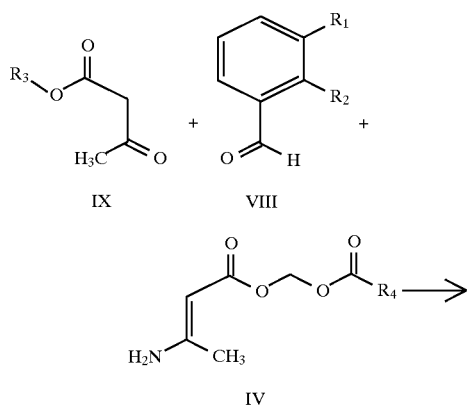

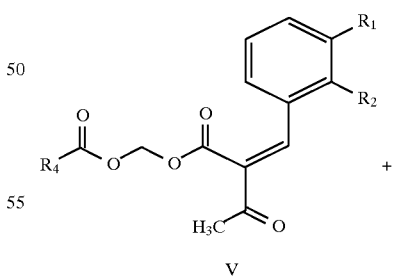

wherein $R_1$–$R_4$ have the same meaning as described above.

Method F:

The compounds of the present invention (I) can be prepared by reacting a suitable benzylidene compound (III) with an suitable acetoacetate (VII) in presence of ammonia as outlined below:

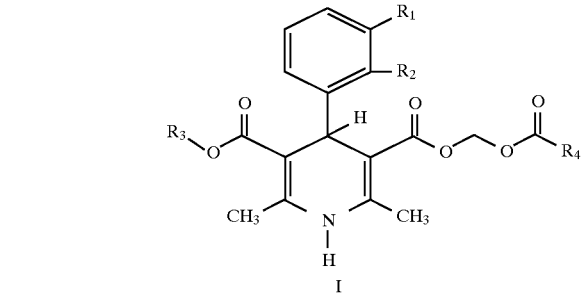

wherein $R_1$–$R_4$ have the same meaning as described above.

Method G:

The compounds of the present invention (I) can be prepared by reacting a suitabel benzylidene compound (V) with an suitable acetoacetate (IX) in presence of ammonia as outlined below:

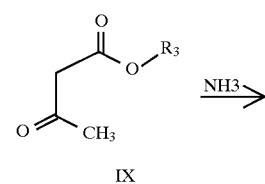

-continued

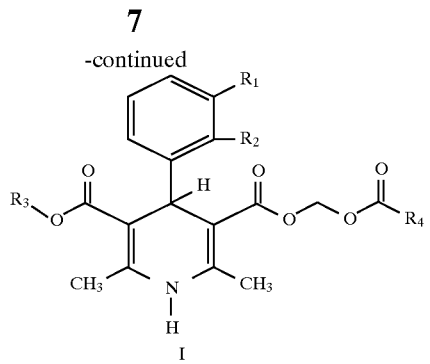

wherein $R_1$–$R_4$ have the same meaning as described above.

Method H:

The compounds of the present invention (I) can be prepared by reacting suitable acetoacetates (VII) and (IX) with an suitable benzaldehyde (VIII) in presence of ammonia as outlined below:

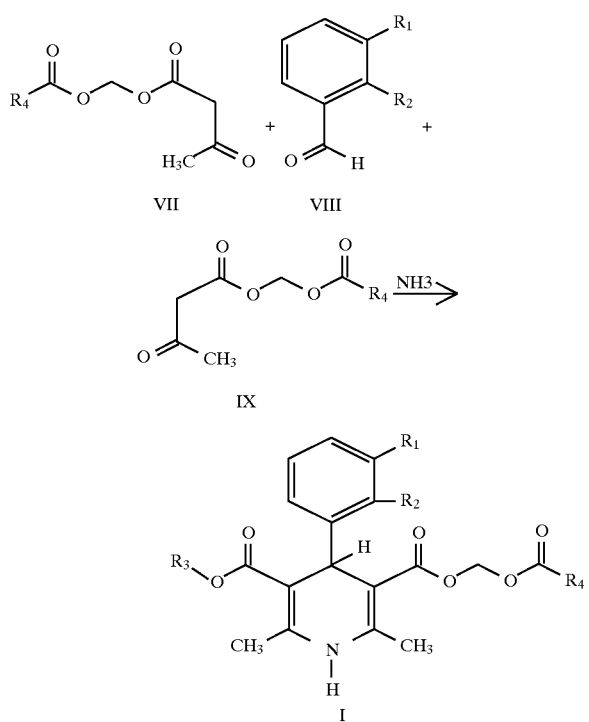

wherein $R_1$–$R_4$ have the same meaning as described above.

In each of the methods A to H the compound obtained can optionally be converted to an optical isomer by known methods.

Pharmaceutical preparations

The compound of formula (I) will normally be administered by injection.

The dosage form may be a liquid solution ready for use or intended for dilution lyophilized or powder filled prior to reconstitution with a suitable vehicle.

The solution may contain cosolvents, surfactants and/or complexing agents in order to increase the solubility of the substance (I).

The solution may also contain other constituents for adjustment of pH, tonicity etc. and may conveniently be provided in various dosage units.

Pharmacological properties

The compounds of the invention (I) show short-acting, potent anti-hypertensive effects. The compounds have been evaluated after intravenous infusion to spontanously hypertensive rats (SHR). The length of the effect duration was determined by stepwise increasing infusion rates during 15 minutes, until the mean arterial blood pressure was reduced to 30 % of the control level. Upon termination of the infusion, the time required for blood pressure normalization (from 70% to 90% of control level) was determined. The so obtained "recovery times", which are a measure of duration of effect, are given in table 1. Potency of the drug have been measured in hypertensive rats by the amount (nmol/kg) required to stepwise lower arterial blood pressure 30% during 15 minutes.

TABLE 1

| R | Recovery time (min) | Potency (nmol/kg) |
|---|---|---|
| methyl | 3.3 | 285 |
| ethyl | 3.4 | 173 |
| (R,S)-propyl | 2.3 | 47 |
| (R)-propyl | 2.6 | — |
| (S)-propyl | 2.8 | — |
| iso-propyl | 2.5 | 76 |
| Sodium nilroprusside | 0.8 | 240 |
| Nicardipine | 35.5 | 26 |
| Felodipine | 30.2 | 26 |

Therapeutic doses in man are to be expected to range from 0.01–100 mg/h.

Conclusions

The test data according to the invention shows that these compounds have antihypertensive effects of very short duration, with recovery times similar to that of sodium nitroprusside, which is the most commonly used drug today for the treatment of per- and post operative hypertension.

The present invention belongs to drugs classified as calcium antagonists, and are as such unlikely to generate toxic metabolites during long-term infusion, which is the case after sodium nitroprusside, which limits the use of the latter drug.

The present invention can thus be regarded as safer and more suitable for the treatment of per- and postoperative blood pressure control than existing therapy.

EXAMPLES

The present invention is illustrated in detail by the following examples but should not be construed to be limited thereto.

Example 1: Acetoxymethyl methyl 4-(2',3-dichlorophenyl)-2,6-dimethyl-1,4-dihydropyridine-3,5-dicarboxylate To a stirred mixture of 1 ,4-dihydro-2,6-dimethyl-4-(2', 3'-dichlorophenyl)-5-carboxymethyl-3-pyridinecarboxylic acid (0.3 g, 0.83 mmol) and sodium bicarbonate (0.14 g, 1.69 mmol) in DMF (15 ml) under nitrogen atmosphere was added chloromethyl acetate (0.137 g, 1.26 mmol). The reaction mixture was heated at 80° C. for 18 h. Workup by evaporation of solvent and addition of water. Extraction with dichloromethane, the extract was dried over sodium sulfate and concentrated. The resulting oil was subjected to flash chromatography [silica gel, dichloromethane - dichloromethane/methanol (9/1) gradient] to give colorless crystals (0.17 g, 48%) mp.144.5°–147.6° C. $^1$H-NMR (CDCl$_3$): 7.30–7.04 (Ar, 3H); 5.97 (s, 1H); 5.73 (d, J=5.5 Hz, 1H); 5.69 (d, J=5.5 Hz, 1H); 5.46 (s, 1H); 3.60 (s, 3H); 2.32 (s, 3H); 2.30 (s, 3H); 2.03 (s, 3H). $^{13}$C-NMR (CDCl$_3$): 169.64; 167.63; 165.81; 147.46; 146.77; 143.85; 132.86; 131.15; 129.83; 128.31; 126.98; 103.97; 101.89; 78.73; 50.93; 38.45; 20.80; 19.86; 19.26.

Example 2: Propionoxymethyl methyl 4-(2',3'-dichlorophenyl)-2,6-dimethyl-1,4-dihydropyridine-3,5-dicarboxylate To a stirred mixture of 1,4-dihydro-2,6-dimethyl-4-(2',3'-dichlorophenyl)-5-carboxymethyl-3-pyridinecarboxylic acid (5 g,14 mmol) and sodium hydride (0.6 g, 14 mmol) in DMF (25 ml) under nitrogen atmosphere was added chloromethyl propionate (1.71 g, 14 mmol). The reaction mixture was heated at 80° C. for 16 h. Workup by evaporation of solvent and addition of water. Extraction with dichloromethane, the extract was dried over sodium sulfate and concentrated. The resulting yellow crystals was subjected to flash chromatography [silica gel, dichloromethane - dichloromethane/methanol (9/1) gradient] to give pale yellow crystals (2.21 g, 36%), mp.123.8°–125.5° C. $^1$H-NMR (CDCl$_3$): 7.30–7.03 (Ar, 3H); 5.97 (s, 1H); 5.75 (d, J=5.5 Hz, 1H); 5.72 (d, J=5.5 Hz, 1H); 5.46 (s, 1H); 3.60 (s, 3H); 2.34–2.25 (m, 8H); 1.09 (t, J=7.5 Hz, 3H). $^{13}$C-NMR (CDCl$_3$): 173.11; 167.65; 165.83; 147.47; 146.70; 143.87; 132.86; 131.14; 129.83; 128.30; 126.96; 103.95; 101.94; 78.70; 50.92; 38.45; 27.25; 19.86; 19.25; 8.61.

Example 3: Butyroxymethyl methyl 4-(2',3'-dichlorophenyl)-2,6-dimethyl-1,4-dihydropyridine-3,5-dicarboxylate To a stirred mixture of 1,4-dihydro-2,6-dimethyl-4-(2',3'-dichlorophenyl)-5-carboxymethyl-3-pyridinecarboxylic acid (2.62 g, 7.35 mmol) and sodium bicarbonate (1.26 g, 15 mmol) in DMF (130 ml) under nitrogen atmosphere was added chloromethyl butyrate (1.53 g, 11.21 mmol). The reaction mixture was heated at 80° C. for 24 h. Workup by filtration followed by evaporation of solvent. The crude residue was chromatographed on silica gel with 45% ethyl acetate in isooctane. Recrystallization from diisopropylether gave colorless crystals (2.20 g, 66%), mp. 136.2°–138.5° C. $^1$H-NMR (CDCl$_3$): 7.30-7.03 (m, 3H); 5.89 (s, 1H); 5.74 (d, J=5.5 Hz, 1H); 5.70 (d, J=5.5 Hz, 1H); 5.46 (s, 1 H); 3.60 (s, 3H); 2.33 (m, 8H); 1.65-1.55 (m, 2H); 0.90 (t, J=7.4 Hz, 3H).$^{13}$C-NMR (CDCl$_3$): 172.25; 167.61; 165.80; 147.43; 146.59; 143.82; 132.89; 131.11; 129.82; 128.30; 126.95; 103.97; 101.99; 78.63; 50.92; 38.49; 35.79; 19.91; 19.30; 18.01; 13.50.

Example 4: (4S)-Butyroxymethyl methyl 4-(2',3'-dichlorophenyl)-2,6-dimethyl-1,4-dihydropyridine-3,5-dicarboxylate To a stirred mixture of (4R)-1,4-dihydro-2,6-dimethyl-4-(2',3'-dichorophenyl)-5-carboxymethyl-3-pyridinecarboxylic acid (2.93 g, 8.23 mmol) and sodium bicarbonate (1.38 g, 16.5 mmol) in DMF (150 ml) under nitrogen atmosphere was added chloromethyl butyrate (1.72 g, 12.6 mmol). The reaction mixture was heated at 80° C. for 17 h. Workup by filtration followed by evaporation of solvent. The crude residue was chromatographed on silica gel with 5% ethyl acetate in dichloromethane. Recrystallization from diisopropylether gave colorless crystals (2.62 g, 70%), mp. 128°–129° C. NMR spectral data are identical with the data of the racemate as shown in Example 3. $[\alpha]_D^{20}$ =+17.5° (1% in methanol).

Example 5: (4R)-Butyroxymethyl methyl 4-(2',3'-dichlorophenyl)-2,6-dimethyl-1,4-dihydropyridine-3,5-dicarboxylate To a stirred mixture of (4S)-1,4-dihydro-2,6-dimethyl-4-(2',3'-dichorophenyl)-5-carboxymethyl-3-pyridinecarboxylic acid (2.0 g, 5.61 mmol) and sodium bicarbonate (0.96 g, 11.4 mmol) in DMF (100 ml) under nitrogen atmosphere was added chloromethyl butyrate (1.16 g, 8.5 mmol). The reaction mixture was heated at 80° C. for 23 h. Workup by filtration followed by evaporation of solvent. The crude residue was dissolved in dichloromethane and washed with sodium bicarbonatesolution. The organic phase was dried over sodium sulfate and evaporated. Recrystallization first from a mixture of 45% ethylacetate in isooctane followed by diisopropylether gave colorless crystals (1.08 g, 42%), mp. 128°–129° C. NMR spectral data are identical with the data of the racemate as shown in Example 3. $[\alpha]_D^{20}$=–21.50 (1 % in methanol).

Example 6: Isobutyroxymethyl methyl 4-(2',3'-dichlorophenyl)-2,6-dimethyl-1,4-dihydropyridine-3,5-dicarboxylate To a stirred mixture of 1,4-dihydro-2,6-dimethyl-4-(2',3'-dichlorophenyl)-5-carboxymethyl-3-pyridinecarboxylic acid (5.11 g, 14 mmol) and sodium bicarbonate (2.39 g, 28 mmol) in DMF (250 ml) under argon atmosphere was added chloromethyl isobutyrate (2.93 g, 21 mmol). The reaction mixture was heated for 80° C. for 18 h. Workup by evaporation of solvent. The crude residue was dissolved in dichloromethane and washed with sodium bicarbonate-solution. The organic layer was dried and evaporated. The residue was chromatographed on silica gel by gradient eluation (dichloromethane to 25% ethyl acetate in dichloromethane). Recrystallization from diisopropylether gave colorless crystals (3.35, 52%), mp. 145° C. $^1$H-NMR (CDCl$_3$): 7.30-7.04 (m, 3H); 5.73 (d, J=5.5 Hz, 1H); 5.71 (d, J=5.5 Hz, 1H); 5.68 (s, 1H); 5.47 (s, 1 H); 3.60 (s, 3H); 2.49 (m, 1 H); 2.33 (s, 3H); 2.31 (s, 3H); 1.10 (m, 6H). $^{13}$C-NMR (CDCl$_3$): 175.66; 167.62; 165.77; 147.44; 146.47; 143.78; 132.97; 131.24; 129.81; 128.33; 126.93; 103.99; 102.06; 78.89; 50.86; 38.63; 33.69; 19.83; 19.22; 18.55.

We claim:

1. A compound of the formula

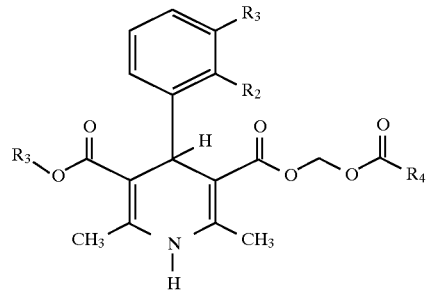

wherein $R_1$ and $R_2$ are independently selected from the group consisting of hydrogen, chloro, bromo, nitro, cyano and trifluoromethyl, and $R_3$ and $R_4$ are independently selected from the group consisting of straight and branched $C_{1-5}$ alkyl groups and including all optical isomers, provided that when $R_3$ is methyl and $R_4$ is tert-butyl, then $R_1/R_2$ are not hydrogen/hydrogen, hydrogen/ 2'-trifluoromethyl, 2'-chloro/3'-chloro, and when $R_3$ is methyl and $R_2/R_1$ is hydrogen/3'-nitro, then $R_4$ is not methyl, ethyl, propyl, iso-propyl or tert-butyl or a pharmaceutically acceptable salt thereof.

2. A compound according to claim 1, selected from
1) Butyroxymethyl methyl 4-(2'3'-dichlorophenyl)2,6-dimethyl-1,4-dihydropyridine-3,5-dicarboxylate
2) (4S)-Butyroxymethyl methyl 4-(2',3'-dichlorophenyl)2,6-dimethyl-1,4-dihydropyridi ne-3 ,5-dicarboxylate
3) (4R)-Butyroxymethyl methyl 4-(2',3'-dichlorophenyl)2,6-dimethyl-1,4-dihydropyridi ne-3 ,5-dicarboxylate
4) iso-Butyroxymathyl methyl 4-(2',3'-dichlorophenyl)-2,6-dimethyl-1,4-dihydropyridine-3,5-dicarboxylate.

3. A process for the preparation of a compound of the formula I as defined in claim 1, wherein a) alkylation of a compound of the formula 11

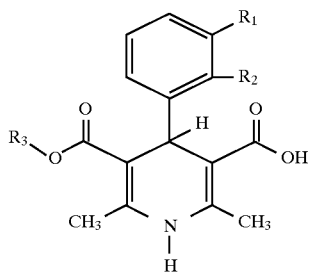
II with a compound of the formula

$R_4COOCH_2X$ in which formulas $R_1$–$R_4$ are defined in claim 1 and X is a standard leaving group, or b) condensation of a compound of the formula III

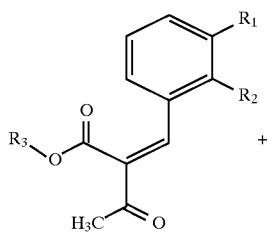
III with an aminocrotonate of the formula IV

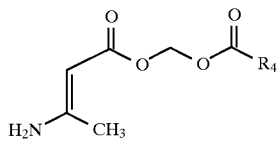
IV in which formulas $R_1$–$R_4$ are as defined in claim 1, or c) condensation of a compound of the formula V

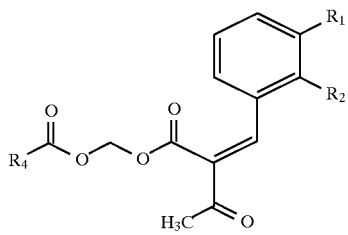
V with an aminocrotonate of the formula VI

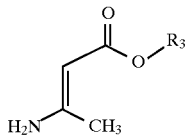
VI in which formulas $R_1$–$R_4$ are defined in claim 1 or d) reaction of a benzaldehyde of the formula VIII

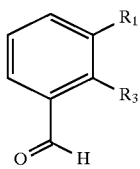
VIII with a acetoacetate of the formula VII

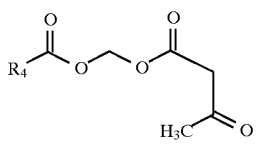
VII and an aminocrotonate of the formula VI

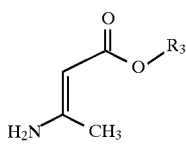
VI in which formulas $R_1$–$R_4$ are as defined in claim 1, or e) reaction of a benzaldehyde of the formula VIII

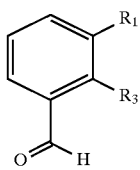
VIII with an acetoacetate of the formula IX

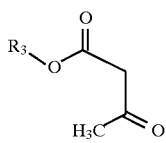
IX and an aminocrotonate of the formula IV

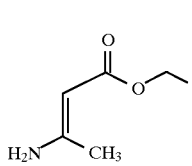
IV in which formulas $R_1$–$R_4$ are as defined in claim 1, or f) reaction of a benzylidene compound of the general formula III

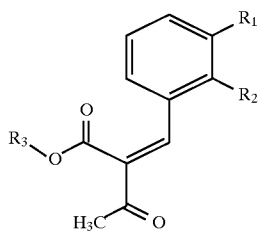

with an acetoacetate of the general formula VII

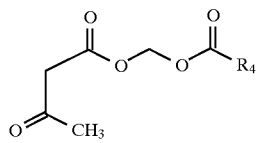

in the presence of ammonia, in which formulas $R_1$–$R_4$ are as defined in claim 1, or g) reaction of a benzylidene compound of the general formula V

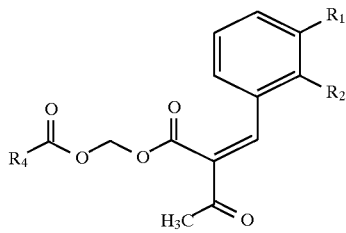

with an acetoacetate of the formula IX

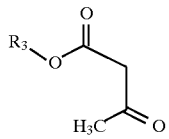

in the presence of ammonia, in which formulas $R_1$–$R_4$ are as defined in claim 1, or h) reaction of acetoacetates of the general formulas VII and IX

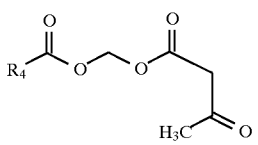

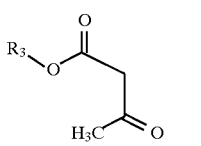

with a benzaldehyde of the general formula VIII

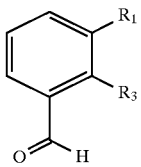

in the presence of ammonia, in which formulas $R_1$–$R_4$ are as defined in claim 1, alternatively wherein the compound obtained by any of the processes a)–h) is converted to an optical isomer thereof by known methods.

4. A process according to claim 3, wherein a compound according to claim 2 is prepared.

5. A pharmaceutical composition comprising an effective amount of a compound according to claim 1 or 2.

6. A pharmaceutical composition according to claim 5 in dosage unit form.

7. A pharmaceutical composition according claim 5 comprising a compound according to claim 1 or 2 in association with a pharmaceutically acceptable carrier.

8. A method for lowering the blood pressure in a host comprising administering to a host in need of such treatment an effective amount of a compound according to claim 1 or 2.

* * * * *

UNITED STATES PATENT AND TRADEMARK OFFICE
CERTIFICATE OF CORRECTION

PATENT NO. : 5,856,346
DATED : Jan. 5, 1999
INVENTOR(S) : Andersson, et al

It is certified that error appears in the above-identified patent and that said Letters Patent is hereby corrected as shown below:

Item [57] in the Abstract, please delete the formula I, and replace with the following new formula:

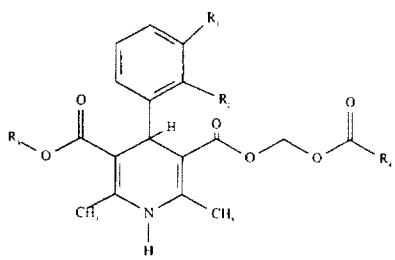

wherein "$R_3$" is replaced with --$R_1$--.

Column 2, please replace the formula I, with the following new formula:

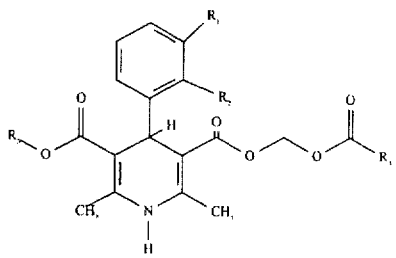

wherein "$R_3$" is replaced with --$R_1$--.

UNITED STATES PATENT AND TRADEMARK OFFICE
CERTIFICATE OF CORRECTION

PATENT NO. : 5,856,346
DATED : Jan. 5, 1999
INVENTOR(S) : Andersson, et al

It is certified that error appears in the above-identified patent and that said Letters Patent is hereby corrected as shown below:

Column 5, please delete the formula VI, and replace with the following formula

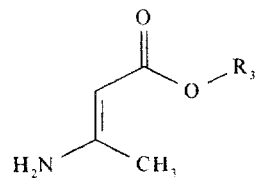

wherein "H₃N" is replace with --H₂N--.

Column 2, line 13, delete "fascilitate" and replace with --facilitate--.

Column 2, line 44, delete "hydrogen13" and replace with --hydrogen/3'--.

Column 4, line 54, after "with" delete "an" and replace with --a--.

Column 5, line 27, delete "wotj an" and replace with --with an--.

Column 6, line 43, delete "suitabel" and replace with --suitable--.

Column 6, line 44, delete "an" and replace with --a--; same line, after "in" insert --the--.

Column 7, line 19, delete "an" and replace with --a--; same line, after "in" insert --the--.

Column 8, in Table 1, after "Sodium" delete "nilroprusside" and replace with --nitroprusside--.

UNITED STATES PATENT AND TRADEMARK OFFICE
CERTIFICATE OF CORRECTION

PATENT NO. : 5,856,346
DATED : Jan. 5, 1999
INVENTOR(S) : Andersson, et al

It is certified that error appears in the above-identified patent and that said Letters Patent is hereby corrected as shown below:

Column 10, Claim 1, please delete the formula I, and replace with the following new formula:

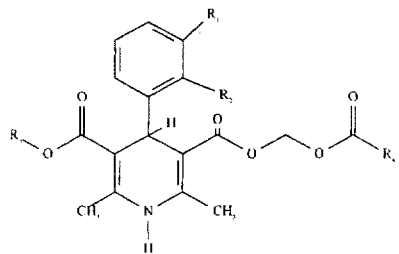

wherein "$R_3$" is replaced with --$R_1$--.

Column 12, Claim 3, please delete the formula VIII, and replace with the following new formula:

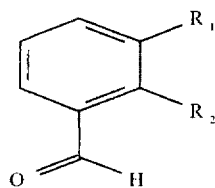

wherein "$R_3$" is replaced with --$R_2$--.

UNITED STATES PATENT AND TRADEMARK OFFICE
CERTIFICATE OF CORRECTION

PATENT NO. : 5,856,346
DATED : Jan. 5, 1999
INVENTOR(S) : Andersson, et al

It is certified that error appears in the above-identified patent and that said Letters Patent is hereby corrected as shown below:

Column 14, Claim 3, please delete the formula VIII, and replace with the following new formula:

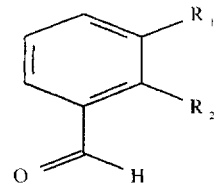

wherein "$R_3$" is replaced with --$R_2$--.

Signed and Sealed this

Seventh Day of September, 1999

Attest:

Q. TODD DICKINSON

Attesting Officer

Acting Commissioner of Patents and Trademarks